United States Patent [19]
Fedorov et al.

[11] Patent Number: 5,480,428
[45] Date of Patent: Jan. 2, 1996

[54] CORRECTIVE INTRAOCULAR LENS

[75] Inventors: Svyatoslav N. Fedorov; Viktor K. Zuev, both of Moscow, Russian Federation

[73] Assignee: Mezhotraslevoi Nauchno-Tekhnichesky Komplex "Mikrokhirurgia Glaza", Moscow, Russian Federation

[21] Appl. No.: 231,549

[22] Filed: Apr. 22, 1994

[30] Foreign Application Priority Data

Apr. 22, 1993 [RU] Russian Federation ............. 93021177

[51] Int. Cl.$^6$ ...................................................... A61F 2/16
[52] U.S. Cl. ........................................................... 623/6
[58] Field of Search ...................................... 623/6

[56] References Cited

U.S. PATENT DOCUMENTS

| | | | |
|---|---|---|---|
| 4,585,456 | 4/1986 | Blackmore | 623/6 |
| 4,769,035 | 9/1988 | Kelman | 623/6 |
| 4,816,032 | 3/1989 | Hetland | 623/6 |
| 4,994,080 | 2/1991 | Shepard | 623/6 |
| 5,258,025 | 11/1993 | Fedorov et al. | 623/6 |

FOREIGN PATENT DOCUMENTS

| | | | |
|---|---|---|---|
| 8902252 | 3/1989 | WIPO | 623/6 |
| 9113597 | 9/1991 | WIPO | 623/6 |

*Primary Examiner*—Randy C. Shay
*Attorney, Agent, or Firm*—Keck, Mahin & Cate

[57] ABSTRACT

An intraocular lens includes a optical body including a posterior concave surface with a first radius of curvature, a periphery and a central, axially aligned opening that enhances liquid circulation in the eye, with the ratio of the height of the optical body to the overall height of the lens being between about 0.25 to about 0.5; a positioning element connected to the optical body periphery and including a periphery and a posterior concave surface with a second radius of curvature greater than the first radius of curvature, a ratio of the first to second radii of curvature being between about 0.31 to about 0.42; and end elements connected with opposite ends of the positioning element, each end element including a proximal end connected with the positioning element periphery, a distal end, a posterior concave surface forming a smooth continuation of the positioning element posterior concave surface and having a curvature identical therewith, and an anterior surface on an opposite side of the end element, the end element anterior surface having a substantially linear slope such that the end element decreases in thickness from the proximal end to the distal end, and the intraocular lens having an outer dimension defined by the distal ends of the end elements which prevents anchoring of the intraocular lens in an eye and thereby permits floating of the intraocular lens in the eye.

10 Claims, 1 Drawing Sheet

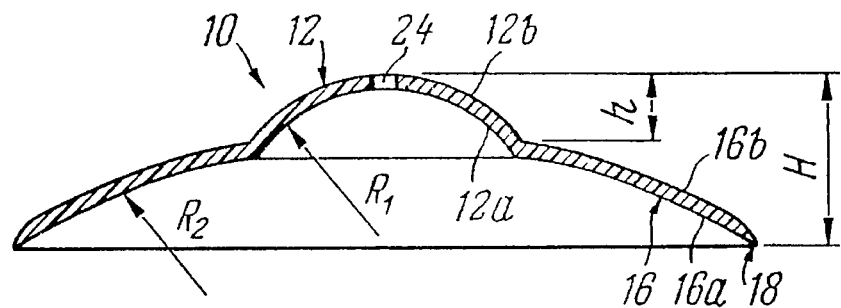
FIG. 2
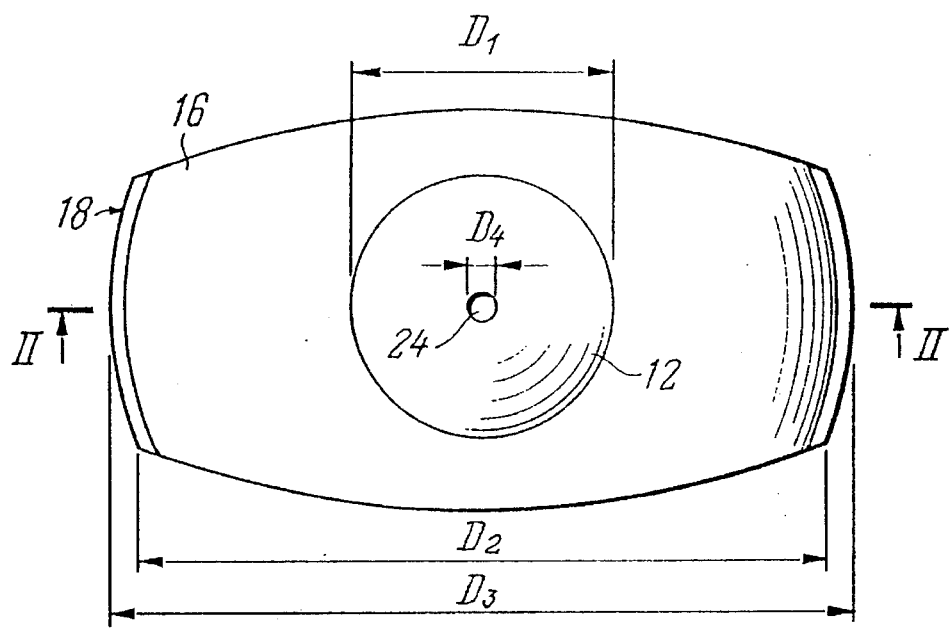
FIG. 1
FIG. 3
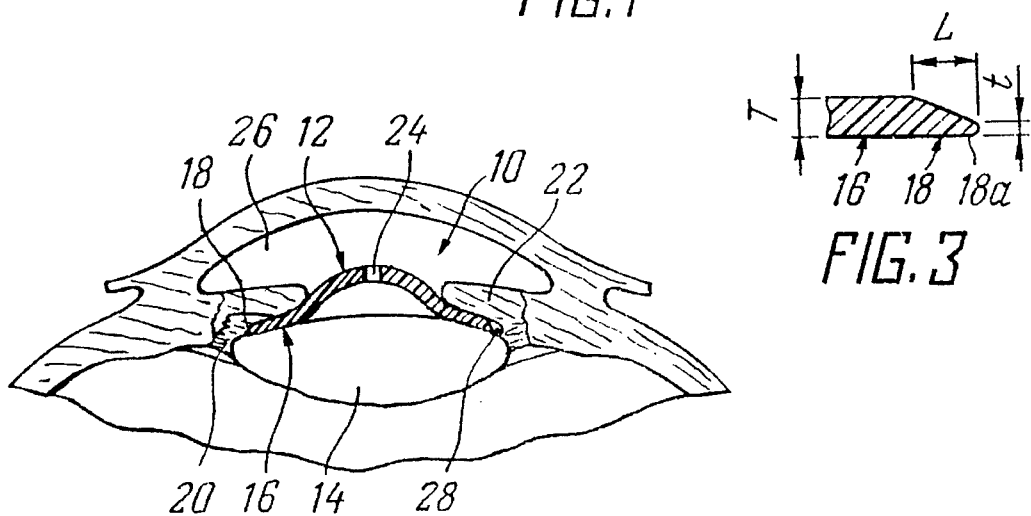
FIG. 4

CORRECTIVE INTRAOCULAR LENS

BACKGROUND OF THE INVENTION

1. Field of the Invention

The present invention relates generally to medicine, and more specifically to ophthalmology, and has particular reference to a corrective intraocular lens which finds successful application for treatment of myopia, hyperopia, astigmatism, and other eye diseases.

2. Description of the Prior Art

Correction of such eyesight deficiencies as myopia, hyperopia, and the like has conventionally involved the use of glasses or contact lenses. However, correction with the use of such devices is temporary, since such devices must be placed and removed periodically, for example, while skiing, swimming and the like.

Permanent correction of eyesight is performed with the aid of keratotomy. One of these techniques includes removal of the corneal layer and its reshaping, while another technique includes the making of a multiplicity of radial cuts into the corneal layer to adjust the curvature thereof, followed by healing. The aforesaid kerato-refractive surgical techniques are of an irreversible nature and suffer from inadequate accuracy of prognostication of the postoperative refractive effect.

Intraocular lenses or lenticuli have been used to solve these problems, but they are intended largely for correction of postcouching aphakia.

There has been provided a corrective lens for use in conjunction with the intact natural lens, such as that described in U.S. Pat. No. 4,585,456 issued on Apr. 29, 1986 to Blackmore. This corrective lens employs an optical body formed of a material biocompatible with the eye and having a concave posterior surface with a curvature that fits the curvature of the external surface of the natural lens. The aforesaid optical body includes a means for positioning it so that it is adjacent to the natural lens. To retain the corrective lens in this position, provision is made for supporting elements shaped as, for example, open loops associated with the positioning means as is known in the art with respect to intraocular lenses. When inserting such a corrective lens within the patient's eye, the supporting elements are placed in the ciliary sulcus. However, such an attachment is subject to various disadvantages inherent in fastening of an intraocular lens in the ciliary sulcus and, in particular, the rather frequent danger-of inflammation of the ocular tissues. Moreover, as it has been confirmed by practical experience, such an attachment might be inadequately reliable and results in dislocation or displacement of the corrective lens.

There is known in the prior art an intraocular lens which includes an optical body having a posterior concave surface, an anterior surface and a periphery. The lens further includes a positioning element in surrounding relation to the optical body and connected to the periphery thereof, the positioning element including a periphery and a posterior concave surface that forms a smooth continuation of the optical body posterior concave surface and which has a curvature identical to the curvature of the optical body posterior concave surface. Finally, the lens includes a supporting element including a proximal portion connected with the positioning element periphery, a distal portion adapted to contact a zonal ligament, a posterior concave surface on one side of the supporting element between the proximal portion thereof and the distal portion, the supporting element posterior concave surface forming a smooth continuation of the positioning element posterior concave surface and having a curvature identical to the curvature of the positioning element posterior concave surface. The supporting element further includes an anterior surface on an opposite side of the supporting element between the proximal portion and the distal portion thereof, the supporting element anterior surface having a concavity which has an opposite direction of curvature from the supporting element posterior concave surface, such that the supporting element non-linearly decreases in thickness between the supporting element anterior surface and the supporting element posterior concave surface, from the proximal portion to the distal portion thereof.

However, with such corrective lens for use in conjunction with the intact natural lens, the lens is secured to the zonal ligaments. As a result, the lens is at a fixed position in the eye. However, in some instances, the pupil of the eye may be off-center, for example, offset upwardly and toward the nose. Although this lens functions well when the pupil of the person is centered in the eye, this lens does not function as well when the pupil is off-center. This is because the lens is fixed to the zonal ligaments at a predetermined position in the eye. In such case, the corrective lens is fixed and can only contract and expand.

Further, because the lens is fixed in the eye, it is limited to a relatively small range of diopters, and has, for example, an upper limit of use with a −12 diopter.

Still further, with the aforementioned corrective lens, because there is a thickened portion at the intersection of the positioning element with the optical body, when the lens is inserted in the eye, a force is applied to the iris. As a result, the iris is biased into a substantially frusto-conical configuration. This is disadvantageous, and rather, it is desirable that the iris remain in its original substantially planar configuration.

Also, with corrective lenses that are fixed in the eye, it is necessary to remove portions of the iris in order to provide circulation of liquid in the eye, which is essential to normal operation of the eye.

SUMMARY OF THE INVENTION

Accordingly, it is an object of the present invention to provide a corrective lens for use with the natural crystalline lens of the eye.

It is another object of the present invention to provide such a corrective lens which floats in the eye.

It is still another object of the present invention to provide such a corrective lens which thereby follows the pupil of the eye at all times.

It is yet another object of the present invention to provide such a corrective lens in which the iris is maintained in a substantially planar configuration.

It is a further object of the present invention to provide such a corrective lens which enables circulation of liquid in the eye without removing any portion of the iris.

It is a still further object of the present invention to provide such a corrective lens which can be used with a wide range of diopters from about 0 to about −25, and with a preferred practical range of about −10 to about −25.

It is a yet further object of the present invention to provide such a corrective lens that is relatively easy to manufacture and easy to insert.

In accordance with an aspect of the present invention, an intraocular lens for use with a natural crystalline lens of an eye, the eye having an iris, includes optical body means for centering the intraocular lens in the iris of the eye, the optical body means having a periphery; and positioning means for supporting the intraocular lens in a floating manner on the natural crystalline lens of the eye, the positioning means being connected with the periphery of the optical body means.

Specifically, the optical body means has a posterior concave surface with a radius of curvature, and dimensions that permit the optical body to fit within the iris of the eye; and the positioning means includes a posterior concave surface that conforms to the natural crystalline lens of the eye.

At least one end element is connected at opposite ends of the positioning element, each end element including a posterior concave surface forming a smooth continuation of the posterior concave surface of the positioning means and decreasing in thickness in a direction away from the positioning means; and the intraocular lens having an outer dimension which prevents anchoring of the intraocular lens in an eye such that the positioning means and the at least one end element float on the natural crystalline lens and the optical means is centered in the iris.

The optical means further includes opening means for providing circulation of liquid in the eye, the opening means being positioned substantially centrally of the optical means.

In accordance with another aspect of the present invention, an intraocular lens for use with a natural crystalline lens of an eye, includes an optical body through which vision occurs, the optical body having a periphery and opening means for providing circulation of liquid in the eye, the opening means being positioned substantially centrally of the optical body; and positioning means for supporting the intraocular lens on the natural crystalline lens of the eye, the positioning means being connected with the periphery of the optical body.

Preferably, the opening has a diameter in the range of about 0.4 mm to about 0.5 mm.

In accordance with still another aspect of the present invention, an intraocular lens for use with a natural crystalline lens of an eye, the eye having an iris, includes an optical body including a posterior concave surface with a first radius of curvature, and a periphery; a positioning element in surrounding relation to the optical body and connected to the periphery of the optical body, the positioning element including a periphery and a posterior concave surface with a second radius of curvature greater than the first radius of curvature; and end elements connected with opposite ends of the positioning element, each end element including a proximal end connected with the periphery of the positioning element, a distal end, a posterior concave surface which forms a smooth continuation of, and has a curvature identical to, the posterior concave surface of the positioning element, and an anterior surface having a slope such that the end element decreases in thickness from the proximal end to the distal end; and the intraocular lens having an outer dimension defined by the distal ends of the end elements which prevents anchoring of the intraocular lens in an eye such that the positioning element and the at least one end element float on the natural crystalline lens and the optical body is centered in the iris.

Each of the optical body and the positioning element has a substantially constant thickness.

Further, the optical body has an opening extending therethrough. The opening extends along an axial direction of the optical body and is substantially centrally positioned on the optical body.

In addition, the anterior surface of each end element has a substantially linear slope.

In accordance with yet another aspect of the present invention, an intraocular lens for use with a natural crystalline lens of an eye, the eye having an iris, and the intraocular lens having an overall height, includes a part spherical optical body including a posterior concave surface with a first radius of curvature, and a periphery, the optical body having a height, with a ratio of the height of the optical body to the overall height being in the range of about 0.25 to about 0.5; a part spherical positioning element in surrounding relation to the optical body and connected to the periphery of the optical body, the positioning element including a periphery, and a posterior concave surface with a second radius of curvature greater than the first radius of curvature, a ratio of the first radius of curvature to the second radius of curvature being within a range of about 0.31 to about 0.42; and end elements connected with opposite ends of the positioning element, each end element including a proximal end connected with the periphery of the positioning element, a distal end, a posterior concave surface forming a smooth continuation of, and having a curvature identical to, the posterior concave surface of the positioning element, and an anterior surface having a slope such that the end element decreases in thickness from the proximal end to the distal end; and the intraocular lens having an outer dimension defined by the distal ends of the end elements which prevents anchoring of the intraocular lens in an eye such that the positioning element and the end elements float on the natural crystalline lens and the optical body is centered in the iris.

Preferably, the optical body has an outer diameter in the range of about 4.0 mm to about 5.5 mm, and the opening is circular and has a diameter in the range of about 0.4 mm to about 0.5 mm. Further, the positioning element has an outer dimension in the range of about 9.4 mm to about 10.2 mm. In addition, each end element has a thickness of about 0.1 mm at the proximal end thereof, a thickness of about 0.01 mm at the distal end thereof, and a length of about 0.3 mm.

In accordance with a further aspect of the present invention, an intraocular lens for use with a natural crystalline lens of an eye, the eye having an iris, and the intraocular lens having an overall height, includes a part spherical optical body having an outer diameter in the range of about 4.0 mm to about 5.5 mm and having a height, with a ratio of the height of the optical body to the overall height being in the range of about 0.25 to about 0.5, and the optical body including a posterior concave surface with a first radius of curvature, a periphery, and a circular opening extending therethrough along an axial direction of the optical body and substantially centrally positioned on the optical body, the opening having a diameter in the range of about 0.4 mm to about 0.5 mm; a part spherical positioning element in surrounding relation to the optical body and connected to the periphery of the optical body, the positioning element including a periphery having an outer dimension in the range of about 9.4 mm to about 10.2 mm, and a posterior concave surface with a second radius of curvature greater than the first radius of curvature, a ratio of the first radius of curvature to the second radius of curvature being within a range of about 0.31 to about 0.42; and end elements connected with opposite ends of the positioning element, each end element including a proximal end connected with the periphery of the positioning element, a distal end, a posterior concave surface forming a smooth continuation of, and having a curvature identical to, the posterior concave surface of the positioning element, and an anterior surface having a substantially linear slope such that the end element decreases in thickness from the proximal end to the distal end; and the intraocular lens having an outer dimension defined by the distal ends of the end elements which prevents anchoring of the intraocular lens in an eye such that the positioning element and the end elements float on the natural crystalline lens and the optical body is centered in an iris of an eye.

BRIEF DESCRIPTION OF THE DRAWINGS

FIG. 1 is a plan view of a corrective lens according to the present invention;

FIG. 2 is a cross-sectional view of the corrective lens of FIG. 1, taken along line 2—2 thereof;

FIG. 3 is a cross-sectional view of an end of the Corrective lens of FIG. 1; and FIG. 4 is a cross-sectional view of an eye with the corrective lens of FIG. 1 inserted therein.

DESCRIPTION OF THE PREFERRED EMBODIMENT

Referring now to FIGS. 1 and 2, there is shown a corrective lens 10 according to the present invention which is intended for correction of a phakic eye. Such a lens can be produced by molding from a material such as polymethyl-methacrylate, silicone rubber, polyhydroxyethyl-methacrylate, the copolymer of silicone and methyl-methacrylate, polyvinylpyrrolidone, and other materials which are biocompatible with the ocular tissue and aqueous humor and preferably hydrophilic and/or permeable to oxygen.

Corrective lens 10 includes a part spherical optical body 12 having a concave posterior surface 12a and an anterior surface 12b of the same curvature. Therefore, the thickness of optical body 12 is substantially uniform or constant throughout. Posterior surface 12a is located on the side corresponding to the outer surface of the natural crystalline lens 14 (FIG. 4) and has a radius R1 of curvature which is preferably within the range of about 3.0 to about 3.5 mm. Further, optical body 12 preferably has an outer diameter D1 in the range of about 4.0 to about 5.5 mm.

Optical body 12 is encompassed and integrally formed along its entire circumference by a part spherical positioning element 16, having a posterior concave surface 16a with a radius R2 of curvature equal to the radius of curvature of the outer surface of natural crystalline lens 14, as shown in FIG. 4. The radius R2 of curvature preferably ranges between about 9.0 and 10.0 mm. Positioning element 16 also has an anterior surface 16b of the same curvature as posterior surface 16a, and therefore, the thickness of positioning element 16 is substantially uniform or constant throughout. Positioning element 16 serves to set optical body 12 in the eye on the outer surface of the intact natural crystalline lens 14 in the course of orienting optical body 12 with respect to the natural crystalline lens. Positioning element 16 preferably has an outer dimension D2 which ranges from about 9.4 mm to about 10.2 mm.

End elements 18 are formed at opposite ends of positioning element 16 and are thinned as compared with positioning element 16, as can be seen from the enlarged cross-sectional view of FIG. 3. Preferably, the inner thickness T of each end element 18 is equal to about 0.1 mm (which is the same thickness as positioning element 16 and optical body 12), while the outer thickness t of each end element 18 at its peripheral surface is about 0.01 mm. However, the edge of the end portion must not be excessively sharp for fear of injuring the eye tissue with the edge. Taking account of the fact mentioned above, it is expedient to make the thinning along a substantially linear generant on the side of the anterior surface 18b of each end element 18. The posterior surface 18a of each end element 18 has the same radius R2 of curvature as the posterior surface 16a of positioning element 16. The distance D3 between the diametrically opposite ends of end elements 18 preferably ranges from about 10.0 mm to about 10.8 mm. In other words, each end element 18 preferably has a length L of about 0.3 mm. It will therefore be appreciated that this range is less than the diametric distance between the Zinn's zonules or Zinn ligaments 20 (FIG. 4), so that lens 10 is free to float in the eye.

It is important that certain parameters be satisfied in order for the lens 10 to correctly fit within the eye. Thus, it is important that the ratio of the height h of optical body 12 over the overall height H of lens 10 be in the range of about 0.25 to about 0.5, that is, h/H=0.25~0.5. Further, it is important that the ratio of radius R1 to radius R2 be in the range of about 0.31 to about 0.42, that is, R1/R2=0.31~0.42.

Accordingly, with the present invention described above, a corrective lens 10 for use with the natural crystalline lens 14 of the eye is provided so as to float in the eye. As a result, corrective lens 10 thereby follows the pupil of the eye at all times, regardless of the same being offset or eccentric. In other words, intraocular lens 10 has an outer dimension defined by the distal ends of end elements 18 which prevents anchoring of intraocular lens 10 in an eye such that positioning element 16 and end elements 18 float on the natural crystalline lens 14, and such that optical body 12 is centered in iris 22 of an eye. Further, as shown in FIG. 4, the iris 22 is maintained in a substantially planar configuration, as with the natural eye.

In the situation where the iris 22 contracts, for example, in the presence of a strong light, optical body 12 will still remain centered within iris 22. However, in such case, iris 22 will ride up along the surface of optical body 22 so that the iris will be inclined outwardly.

In accordance with a further aspect of the invention, optical body 12 is provided with an central, axially aligned opening 24 therein. Opening 24 preferably has a diameter D4 in the range of about 0.4 mm to about 0.5 mm. By providing opening 24, there is always proper circulation of liquid in the eye, and there is no need to remove any portion of iris 22 to provide such circulation. It is noted that, because of the focusing of light from other portions of optical body 12, the wearer of the lens 10 will not notice any defect in the produced image from opening 24. At most, there will be a slight darkening of the image, which also will not be noticed by the wearer of lens 10.

The above-described corrective lens 10 can be used in a wide range of diopters from about 0 to about −25. From a practical standpoint, the range of use of corrective lens 10 will be with diopter values ranging from about −10 to about −25.

The proposed corrective lens is positioned as follows.

Under local anesthesia, an incision into the cornea or limbus is made to establish an access to an anterior eye chamber 26 (FIG. 4). Then, corrective lens 10 is introduced, using forceps, through the preliminary dilated pupil, into posterior eye chamber 28 at 6 o'clock, and then at 12 o'clock. Next, corrective lens 10 is adjusted for position by moving it with its posterior concave surface 16a over the outer surface of intact natural crystalline lens 14. As a result of this positioning, optical body 12 is arranged on the eye optic axis within the opening in iris 22. On completion of surgery, the operative incision is stitched up.

While a preferred embodiment of the invention has been disclosed herein, it will be understood that various modifications and versions may occur to those skilled in the art without departing from the spirit and scope of the present invention as defined by the claims that follow.

What is claimed is:

1. An intraocular lens for use with a natural crystalline lens of an eye, the eye having an iris, and said intraocular lens having an overall height, said intraocular lens comprising:

a part spherical optical body including a posterior concave surface with a first radius of curvature, and a periphery, said optical body having a height, with a ratio of the height of said optical body to said overall height being in the range of about 0.25 to about 0.5;

a part spherical positioning element in surrounding relation to the optical body and connected to the periphery of the optical body, said positioning element including a periphery, and a posterior concave surface with a second radius of curvature greater than said first radius of curvature, a ratio of said first radius of curvature to said second radius of curvature being within a range of about 0.31 to about 0.42; and end elements connected with opposite ends of said positioning element, each end element including a proximate end connected with the periphery of the positioning element, a distal end, a posterior concave surface forming a smooth continuation of, and having a curvature identical to, the posterior concave surface of said positioning element, and an anterior surface having a slope such that said end element decreases in thickness from said proximal end to said distal end; and said intraocular lens having an outer dimension defined by the distal ends of said end elements which prevents anchoring of said intraocular lens in an eye such that said positioning element and said end elements float on the natural crystalline lens and said optical body is centered in the iris.

2. An intraocular lens according to claim 1, wherein each of said optical body and said positioning element has a substantially constant thickness.

3. An intraocular lens according to claim 1, wherein said optical body has an opening extending therethrough.

4. An intraocular lens according to claim 3, wherein said opening extends along an axial direction of said optical body and is substantially centrally positioned on said optical body.

5. An intraocular lens according to claim 3, wherein said optical body has an outer diameter in the range of about 4.0 mm to about 5.5 mm, and said opening is circular and has a diameter in the range of about 0.4 mm to about 0.5 mm.

6. An intraocular lens according to claim 1, wherein said positioning element has an outer dimension in the range of about 9.4 mm to about 10.2 mm.

7. An intraocular lens according to claim 1, wherein said anterior surface of each said end element has a substantially linear slope.

8. An intraocular lens according to claim 1, wherein each said end element has a thickness of about 0.1 mm at the proximal end thereof and a thickness of about 0.01 mm at the distal end thereof.

9. An intraocular lens according to claim 1, wherein each said end element has a length of about 0.3 mm.

10. An intraocular lens for use with a natural crystalline lens of an eye, the eye having an iris, and said intraocular lens having an overall height, said intraocular lens comprising:

a part spherical optical body having an outer diameter in the range of about 4.0 mm to about 5.5 mm and having a height, with a ratio of the height of said optical body to said overall height being in the range of about 0.25 to about 0.5, and said optical body including a posterior concave surface with a first radius of curvature, a periphery, and a circular opening extending therethrough along an axial direction of said optical body and substantially centrally positioned on said optical body, said opening having a diameter in the range of about 0.4 mm to about 0.5 mm;

a part spherical positioning element in surrounding relation to the optical body and connected to the periphery of the optical body, said positioning element including a periphery having an outer dimension in the range of about 9.4 mm to about 10.2 mm, and a posterior concave surface with a second radius of curvature greater than said first radius of curvature, a ratio of said first radius of curvature to said second radius of curvature being within a range of about 0.31 to about 0.42; and end elements connected with opposite ends of said positioning element, each end element including a proximal end connected with the periphery of said positioning element, a distal end, a posterior concave surface forming a smooth continuation of, and having a curvature identical to, the posterior concave surface of said positioning element, and an anterior surface having a substantially linear slope such that said end element decreases in thickness from said proximal end to said distal end; and said intraocular lens having an outer dimension defined by the distal ends of said end elements which prevents anchoring of said intraocular lens in an eye such that said positioning element and said end elements float on the natural crystalline lens and said optical body is centered in an iris of an eye.

* * * * *